(12) United States Patent
Baralt et al.

(10) Patent No.: US 6,734,329 B1
(45) Date of Patent: May 11, 2004

(54) OLIGOMERIZATION OF ALPHA OLEFINS IN THE PRESENCE OF CARBOXYLIC ACIDS

(75) Inventors: Eduardo J. Baralt, Kingwood, TX (US); Russell Bak, The Woodlands, TX (US)

(73) Assignee: Chevron U.S.A. Inc., Ramon, CA (US)

( * ) Notice: Subject to any disclaimer, the term of this patent is extended or adjusted under 35 U.S.C. 154(b) by 0 days.

(21) Appl. No.: 09/678,413

(22) Filed: Oct. 2, 2000

(51) Int. Cl.[7] .............................. C07C 2/04; C07C 2/24; C07C 2/34
(52) U.S. Cl. ................... 585/510; 585/520; 585/525; 585/511
(58) Field of Search .................. 585/510, 520, 585/525, 511

(56) References Cited

U.S. PATENT DOCUMENTS

| | | | | |
|---|---|---|---|---|
| 3,769,363 A | | 10/1973 | Brennan | 260/683.15 B |
| 3,997,621 A | | 12/1976 | Brennan | 260/683.15 B |
| 4,045,507 A | * | 8/1977 | Cupples et al. | 260/683.15 B |
| 4,436,947 A | | 3/1984 | Morganson et al. | 585/525 |
| 5,191,140 A | | 3/1993 | Akatsu et al. | 585/525 |
| 5,396,013 A | | 3/1995 | Theriot | 585/510 |
| 5,929,297 A | | 7/1999 | Theriot et al. | 585/525 |

FOREIGN PATENT DOCUMENTS

| | | | |
|---|---|---|---|
| JP | 73023405 B | | 7/1973 |
| JP | 73023405 B | * | 7/1973 |

* cited by examiner

Primary Examiner—Walter D. Griffin
Assistant Examiner—Tam M. Nguyen
(74) Attorney, Agent, or Firm—Conley Rose, PC; Rodney B. Carroll; Joe D. Hulett

(57) ABSTRACT

In process for the oligomerization of an alphaolefin, a carboxylic acid modifier, such as acetic acid, is used to increase the amount of trimer and tetramer in the product.

9 Claims, No Drawings

OLIGOMERIZATION OF ALPHA OLEFINS IN THE PRESENCE OF CARBOXYLIC ACIDS

FIELD OF THE INVENTION

The present invention relates to a process for the oligomerization of alpha olefins in the presence of a boron trifluoride/alcohol catalyst with a carboxylic acid used as a modifier to increase the amount of trimer and tetramer in the product.

BACKGROUND OF THE INVENTION

The oligomerization of alpha olefins in the presence of a Lewis acid catalyst has been used commercially to produce synthetic fluids which are useful for various commercial applications, such as in synthetic lubrication oils, drilling fluids, hydraulic fluids, and heat transfer fluids. The catalyst of choice is usually boron trifluoride combined with a protic promoter, such as butanol or water. See, for example U.S. Pat. Nos. 4,956,512 and 5,945,574. U.S. Pat. No. 3,769,363 describes the use of an oligomerization catalyst containing boron trifluoride with a carboxylic acid having more than three carbon atoms in the molecule as the promoter. In order to control the degree of oligomerization and increase the amount of trimer in the product, U.S. Pat. No. 3,997,621 teaches the use of an ester in the reaction mixture as a modifier. By controlling the degree of oligomerization the resulting product will have a narrower range of carbon atoms in the molecule which results in more controlled volatility and temperature viscometrics. Generally speaking, it is desirable to produce a product having low volatility and low viscosity for use in crankcase oils.

Surprisingly, it has been found that carboxylic acids may be used as a modifier in the oligomerization reaction of alpha olefins to increase the yields of trimer and tetramer in the product when used in combination with a boron trifluoride/alcohol catalyst complex.

SUMMARY OF THE INVENTION

The present invention is directed to an improved process for controlling the oligomerization of an alpha olefin in the presence of a catalyst complex comprising boron trifluoride and an alcohol to form a polyalphaolefin product, the improvement comprising including with the catalyst complex in the reaction zone containing the catalyst complex and the alpha olefin a sufficient amount of a carboxylic acid modifier to significantly increase -the amount of trimer and tetramer present in the polyalphaolefin product formed as compared to an oligomerization process in which the carboxylic acid is not present, wherein the carboxylic acid contains from 2 to about 10 carbon atoms. The alpha olefin monomer may contain anywhere from 3 to about 22 carbon atoms in the molecule but will preferably contain from 3 to about 14 carbon atoms in the molecule. The oligomerization reaction will proceed over a broad temperature range but is usually carried out in the temperature range of from about 30° C. to about 150° C. and most preferably within the temperature range of from about 40° C. to about 60° C. Following oligomerization the product may be left unsaturated or it may be hydrogenated to saturate the double bonds remaining in the molecule depending on the application for which the product is to be used.

DETAILED DESCRIPTION OF THE INVENTION

The carboxylic acid used as a modifier according to the present invention should contain from 2 to about 10 carbon atoms in the molecule. The carboxylic acid may contain unsaturated carbon to carbon bonds and the carbon chain may be either branched or unbranched. Examples of suitable modifiers include, but are not necessarily limited to, acetic acid, propionic acid, butyric acid, valeric acid, caproic acid, enanthic acid, caprylic acid, pelargonic acid, and capric acid. Particularly preferred for carrying out the invention is acetic acid.

The amount of carboxylic acid present in the oligomerization mixture should be at least a sufficient amount to significantly increase the yield of trimer and tetramer in the final product as compared to an oligomerization mixture which does not contain the carboxylic acid. In general, a significant increase should be at least a 20 weight percent increase in the amount of trimer and tetramer in the product as compared to the oligomerization reaction without the modifier present. The precise amount of carboxylic acid modifier required to practice the invention will vary somewhat depending upon the carboxylic acid chosen, the alpha olefin, the temperature of the reaction mixture, the amount of catalyst, and the ratio of the boron trifluoride to the alcohol promoter. However, these variables merely require the optimization of the conditions of the oligomerization reaction and, as such, should not require any more than routine experimentation which is well within the ability of one skilled in the art.

In general, the amount of carboxylic acid modifier will usually be present within the range of from about 0.08 mole % to about 2.0 mole % of modifier to olefin with about from 0.16 mole % to about 0.35 mole % of modifier being preferred.

The alpha olefin used as the feed for the oligomerization reaction will usually, contain from 3 to about 22 carbon atoms in the molecule and preferably will contain from 3 to about 14 carbon atoms in the molecule. The alpha olefin, of course, will contain an unsaturated carbon to carbon bond in the 1-position, however, the molecule may also contain other internal unsaturated carbon to carbon bonds in the molecule. In addition, the alpha olefin may be either branched or unbranched. However, in most instances when practicing the invention the alpha olefins will be mono-olefinically unsaturated, that is, they will contain only a single double bond in the 1-position, and will be unbranched, that is, the feed will be comprised of a normal alpha olefin. The present invention is most advantageous when the alpha olefin feed is a relatively pure alpha olefin, that is, the feed consists primarily of one alpha olefin as opposed to a mixture of different alpha olefins. Examples of alpha olefins which are suitable for use as feeds in practicing the present invention include propene, 1-butene, 1-pentene, 1-hexene, 1-heptene, 1-octene, 1-decene, 1-dodecene, or 1-teradecene.

The alcohol promoter will be an alcohol having from 1 to about 24 carbon atoms in the molecule, more typically having 12 carbon atoms or less in the molecule. Operable protic promoters include, but are not limited to, methanol, ethanol, 1-propanol, 2-propanol, 1-butanol, 2-methyl-1-propanol, 1-hexanol, and the like. Particularly preferred as a protic promoters are 1-propanol and 1-butanol.

The amount of boron trifluoride used in the reaction mixture is usually in molar excess relative to the amount of the alcohol promoter. The reaction vessel is typically pressurized with boron trifluoride or a mixture of boron trifluoride and nitrogen. The boron trifluoride may be bubbled through the reaction mixture, introduced as part of the catalyst complex, or otherwise introduced into the reaction mixture, as for example, by mechanical stirring.

Although the oligomerization reaction will proceed over a wide temperature range, the reaction preferably is carried out at a temperature in excess of 30° C., and preferably is carried out at a temperature in excess of 40° C. The upper temperature limit is about 150° C., but as a practical matter the oligomerization reaction mixture is usually maintained at a temperature of less than about 60° C.

The following example is used to further illustrate the invention, but it is not intended to a limitation thereon.

EXAMPLE 1

The reactor was sealed and purged with nitrogen. A reaction mixture consisting of 1000 grams of 1-hexene, 0.35 weight percent 1-propanol, and 0.5 weight percent of acetic acid was added to the reactor vessel at a rate of 600 grams per hour. Boron trifluoride was added to the reactor vessel and used to maintain a pressure in the reactor of 30 psi. The reaction mixture was maintained at a temperature of 40 degrees C. After one hour the reaction mixture was washed with caustic water to remove the catalyst. The product was analyzed by gas chromatography. The yield distribution of the product is shown in Table 1 below.

EXAMPLE 2

The procedure of Example 1 was carried out again except without the acetic acid being present. The results of the experiment are shown in Table 1 below.

EXAMPLE 3

The procedure of Example 2 was repeated a second time. The results are shown in Table 1.

TABLE 1

|  | Example 1 | Example 2 | Example 3 |
|---|---|---|---|
| C6 Monomer | 9.65 wt. % | 23.53 wt. % | 10.60 wt. % |
| C12 Olefins | 2.45 wt. % | 1.92 wt. % | 0.24 wt. % |
| C18 Olefins | 44.86 wt. % | 21.60 wt. % | 6.18 wt. % |
| C24 Olefins | 31.19 wt. % | 21.35 wt. % | 18.12 wt. % |
| C30 Olefins | 8.63 wt. % | 15.86 wt. % | 27.96 wt. % |
| C36 Olefins | 3.09 wt. % | 8.50 wt. % | 18.52 wt. % |
| C42 Olefins | 0.13 wt. % | 7.82 wt. % | 18.38 wt. % |

By comparing the yield distribution of products between the three examples, it will be clearly seen that the use of acetic acid as a modifier in Example 1 significantly increased the yield of trimer and tetramer as compared to the controls in Examples 2 and 3 in which no modifier was present.

EXAMPLE 4

The process as described above was repeated using 1-butene as the alpha olefin and propionic, octanoic (caprylic) and decanoic (capric) acid, respectively, as the carboxylic acid modifier. The results of each of the demonstrations was compared to that for acetic acid modifier and are shown in Table 2 below. It should be noted that the amount of trimer present in the product distribution showed a slight increase with the higher carboxylic acids as compared to acetic acid. However, the amount of tetramer and higher oligomers formed were slightly lower when compared with acetic acid.

TABLE 2

| Reference | A | B | C | D | E |
|---|---|---|---|---|---|
| 1-Octene, gr. | 27.4 | 25.5 | 26.9 | 24.5 | 25 |
| 1-Propanol gr. | 2.3 | 2.3 | 2.6 | 2.6 | 2.3 |
| acid |  |  |  |  |  |
| Acid | Acetic | Acetic | Propionic | Octanoic | Decanoic |
| Acid, gr. | 4.8 | 4.4 | 5.8 | 10.1 | 12.8 |
| 1-Butene, gr. | 453.59 | 444.52 | 453.59 | 449.05 | 453.59 |
| wt. % acid to Butene | 1.06 | 0.99 | 1.28 | 2.38 | 2.82 |
| Mole % acid to Butene | 0.99 | 0.92 | 0.97 | 0.93 | 0.92 |
| $BF_3$ consumed, gr. | 26.31 | 25.75 | 24.47 | 20.02 | 27.5 (approx.) |
| Reaction time | 60 min | 60 min | 60 min | 60 min | 60 min |
| Set Temp., ° C. | 20 | 40 | 30 | 45 | 40 |
| Product Distribution, % |  |  |  |  |  |
| C8 | 0.11 | 0.08 | 0.06 | 0.05 | 0.02 |
| C12 | 8.04 | 8.56 | 13.09 | 13.58 | 19.65 |
| C16 | 23.56 | 23.80 | 31.75 | 24.62 | 20.46 |
| C20+ | 68.29 | 67.56 | 55.10 | 61.75 | 59.88 |

EXAMPLE 5

The process as generally described above was repeated using varying amounts of acetic acid. The reaction was allowed to continue for 60 minutes while controlling the temperature at 30° C. The amounts of the modifier and results are shown in Table 3 below.

TABLE 3

| Reference | A | B | C | D | E | F | G |
|---|---|---|---|---|---|---|---|
| Acetic Acid, g | 0 | 0.9 | 1.0 | 5.0 | 8.9 | 11.3 | 23.1 |
| 1-Butene, g | 453.59 | 449.06 | 453.59 | 453.59 | 453.59 | 449.06 | 449.06 |
| Wt. % Acetic Acid:Butene | 0 | 0.2 | 0.22 | 1.10 | 1.96 | 2.52 | 5.15 |
| $BF_3$ Consumed | 17.08 | 15.07 | 18.69 | 26.72 | 30.16 | 36.41 | 51.57 |
| % of C16 in Product | 24.44 | 31.52 | 36.89 | 32.57 | 28.35 | 27.00 | 28.61 |

It will be noted that amount of tetramer in the product increased with an increase in the amount of acetic acid present up to 0.22 wt.% (0.19 mole %) of acetic acid to 1-butene and then began to decrease.

What is claimed is:

1. An improved solvent-free oligomerization process for the oligomerization of an alpha olefin, said process comprises:

charging to an oligomerization reaction zone an oligomerization feed mixture comprising said alpha olefin;

contacting within said oligomerization reaction zone said oligomerization feed mixture with a catalyst complex consisting essentially of boron trifluoride and an alcohol promoter to thereby yield a polyalphaolefin product; and providing a concentration in said oligomerization feed mixture of a modifier consisting essentially of carboxylic acid wherein said concentration is sufficient to significantly increase the yield of trimer and tetramer in said polyalphaolefin product as compared to the yield when there is no said concentration of said modifier, wherein said concentration of said modifier is in the range of from about 0.08 mole percent to about 5.0 mole percent base on the said alpha olefin of said oligomerization feed mixture, wherein the oligomerization process is solvent-free.

2. An improved oligomerization process as recited in claim 1 wherein the carboxylic acid of said modifier is selected from molecules containing from 2 to 10 carbon atoms.

3. An improved oligomerization process as recited in claim 1 wherein said concentration of said modifier is in the range of from about 0.08 mole percent to about 2.0 mole percent based on the said alpha olefin of said oligomerization feed mixture.

4. An improved oligomerization process as recited in claim 3 wherein said concentration of said modifier is in the range of from 0.16 mole percent to 0.35 mole percent based on the alpha olefin of said oligomerization feed mixture.

5. An improved oligomerization process as recited in claim 1 wherein said oligomerization reaction zone during the contacting step is maintained at a temperature in excess of 30° C.

6. An improved oligomerization process as recited in claim 5 wherein said oligomerization reaction zone during the contacting step is maintained at a temperature in the range of from 40° C. to 150° C.

7. An improved oligomerization process as recited in claim 6 wherein said alpha olefin of said oligomerization feed mixture is selected from monounsaturated alpha olefins having from 3 to 22 carbon atoms.

8. An improved oligomerization process as recited in claim 7 wherein said alpha olefin of said oligomerization feed mixture contains from 3 to 14 carbon atoms.

9. An improved oligomerization process as recited in claim 8 wherein said alpha olefin is selected from the group consisting of propene, 1-butene, 1-pentene, 1-hexene, 1-heptene, 1-octene, 1-decene, 1-dodecene, and 1-tetradecene.

* * * * *